United States Patent [19]

Okada et al.

[11] 4,219,670
[45] * Aug. 26, 1980

[54] PROCESS FOR PRODUCING UNSATURATED ALDEHYDES AND UNSATURATED CARBOXYLIC ACIDS

[75] Inventors: Kazuya Okada; Hideo Matsuzawa; Hiromichi Ishii; Masao Kobayashi, all of Otake, Japan

[73] Assignee: Mitsubishi Rayon Company, Limited, Tokyo, Japan

[*] Notice: The portion of the term of this patent subsequent to Jul. 12, 1994, has been disclaimed.

[21] Appl. No.: 886,471

[22] Filed: Mar. 14, 1978

Related U.S. Application Data

[62] Division of Ser. No. 741,508, Nov. 12, 1976, Pat. No. 4,111,985, which is a division of Ser. No. 663,365, Mar. 3, 1976, Pat. No. 4,035,418.

[30] Foreign Application Priority Data

Mar. 12, 1975 [JP] Japan .................................. 50/30313
Mar. 31, 1975 [JP] Japan .................................. 50/39452
Jul. 4, 1975 [JP] Japan .................................. 50/82982

[51] Int. Cl.² .................. C07C 45/04; C07C 47/20; C07C 51/32; C07C 57/04
[52] U.S. Cl. .................................... 562/546; 568/477
[58] Field of Search .................. 260/533 N, 604 R; 562/546

[56] References Cited

U.S. PATENT DOCUMENTS

| 3,642,930 | 2/1972 | Grasselli et al. ................. 260/533 N |
| 4,001,317 | 1/1977 | Grasselli et al. ................. 260/533 N |

*Primary Examiner*—Vivian Garner
*Attorney, Agent, or Firm*—Oblon, Fisher, Spivak, McClelland & Maier

[57] ABSTRACT

An olefin having 4 carbon atoms or t-butyl alcohol is catalytically oxidized in the gas phase with molecular oxygen at 200° to 450° C. to give the corresponding unsaturated aldehyde, unsaturated carboxylic acid and/or conjugated diene in the presence of a catalyst having the formula:

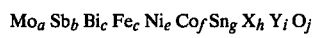

$$Mo_a Sb_b Bi_c Fe_c Ni_e Co_f Sn_g X_h Y_i O_j$$

wherein a to j represent the atomic ratio of each component and a is 12, b is 0.2 to 20, c is 0.2 to 12, d is 0.2 to 12, e is 0.2 to 12, f is 0 to 20, g is 0 to 20, h is 0.01 to 4, i is 0.01 to 4 and j is a value determined by the valencies of the elements in the catalyst, and wherein X is at least one metal selected from the group consisting of potassium, rubidium, cesium and thallium, and Y is at least one metal selected from the group consisting of selenium, tellurium, gallium, vanadium, ruthenium, zinc, niobium, magnesium, chromium, manganese, cadmium and tantalum.

6 Claims, No Drawings

PROCESS FOR PRODUCING UNSATURATED ALDEHYDES AND UNSATURATED CARBOXYLIC ACIDS

This is a division, of application Ser. No. 741,508, filed Nov. 12, 1976, now U.S. Pat. No. 4,111,985 which is a divisional of application Ser. No. 663,365, filed Mar. 3, 1976, now U.S. Pat. No. 4,035,418.

BACKGROUND OF THE INVENTION

1. Field of the Invention

The present invention relates to a process for preparing unsaturated aldehydes, unsaturated carboxylic acids and/or conjugated dienes by the reaction of a suitable starting material over a Mo-Sb-Bi-Fe-Ni type catalyst.

2. Description of the Prior Art

Many processes are known for the gas phase catalytic oxidation of propylene or isobutylene to the corresponding unsaturated aldehyde or acid such as those disclosed in U.S. Pat. Nos. 3,454,630; 3,522,299; 3,576,764; 3,778,386; and 3,825,502. On the other hand Japanese application publication No. 32814/73 shows a process for the catalytic oxidation of t-butyl alcohol to methacrolein at selectivities of 58.0 to 84.1 mole % for methacrolein. Further processes are also known for the catalytic oxidation of butenes to 1,3-butadiene such as disclosed in British Pat. Nos. 1,329,516, and 1,357,848. The disadvantage of these processes is that the selectivity of the conversion of the starting olefin to methacrolein or 1,3-butadiene is insufficient. A need therefore, continues to exist for a catalyst which very effectively promotes the catalytic oxidation of t-butyl alcohol or isobutylene to oxidized products.

SUMMARY OF THE INVENTION

Accordingly, one object of the present invention is to provide a process for preparing methacrolein and methacrylic acid in high yield from isobutylene or t-butyl alcohol.

Another object of the present invention is to provide a process for preparing 1,3-butadiene in high yield from n-butenes.

Yet another object of the present invention is to provide a process for preparing simultaneously, 1,3-butadiene, methacrolein and methacrylic acid in high yield from n-butenes and isobutylene.

Briefly, these objects and other objects of the present invention as hereinafter will become more readily apparent can be attained by a process for catalytically ozidizing at least one compound selected from the group consisting of unsaturated hydrocarbons of 4 carbon atoms and t-butyl alcohol in the gas phase with molecular oxygen at a temperature of 200° to 450° C. to the corresponding unsaturated aldehyde, acid and/or conjugated diene in the presence of a catalyst consisting essentially of

$Mo_aSb_bBi_cFe_dNi_eCo_fSn_gX_hY_iO_j$ wherein X is at least one metal selected from the group consisting of potassium, rubidium, cesium and thallium, Y is at least one metal selected from the group consisting of selenium, tellurium, gallium, vanadium, ruthenium, zinc, niobium, magnesium, chromium, manganese, cadmium and tantalum, and a to j are atomic ratios of each component such that a is 12, b is 0.2 to 20, c is 0.2 to 12, d is 0.2 to 12, e is 0.2 to 12, f is 0 to 20, g is 0 to 20, h is 0.01 to 4, i is 0.01 to 4 and j is a value determined by the valencies of the elements in the catalyst, and wherein, when Y is at least one metal selected from the group consisting of chromium, manganese and cadmium, f is 0.

DESCRIPTION OF THE PREFERRED EMBODIMENTS

The atomic ratios of each component in the catalyst of the present invention can be varied within the ranges mentioned above. A particularly preferred set of ranges of atomic ratios for the elements of the catalyst are such that when a is 12, b=0.5 to 20, c=0.5 to 6, d=0.5 to 6, e=0.5 to 6, f=0.1 to 12, g=0-20, h=0.01 to 2, i=0.01 to 3. Among the metals represented by the symbol X in the catalyst of the present invention, potassium, rubidium and cesium are particularly significant in their ability to promote the activity of the catalyst. Among the metals represented by Y in the catalyst, magnesium, chromium, manganese, zinc, niobium, cadmium and tantalum are preferred components because of their effect on the selectivity of the reaction to the methacrolein and methacrylic acid. If the metal Y is one of those described, cobalt is preferably excluded from the catalyst. If the metal Y is chromium, manganese and/or cadium, cobalt should be excluded from the catalyst.

In the process of the present invention, t-butyl alcohol or isobutylene is catalytically oxidized in the gas phase to yield an oxidized product containing predominantly methacrolein and lesser amounts of methacrylic acid. n-Butenes are catalytically oxidized in the gas phase by the present catalyst to produce 1,3-butadiene.

The preparation of the catalyst used in the present invention can be accomplished by methods well known to those skilled in the art. Any oxide of the elemental components of the catalyst can be used as a starting material or any compound of the elements which are converted to an oxide when it is calcined. Suitable sources of molybdenum include ammonium molybdate, molybdic acid or molybdenum trioxide. Suitable sources of antimony include the oxides, hydrate oxides and chlorides thereof.

In the catalyst of the present invention, antimony has a substantial effect on the reaction and the catalyst efficiency is substantially increased by the addition of antimony. Suitable sources of the other metals include the oxides, nitrates, carbonate, hydroxides and the like.

The catalyst components may be used as they are or supported on such known inert carriers as silica, alumina, silica-alumina or silicon carbide. When the reaction of the present invention is performed, the starting materials used in the reaction include isobutylene, a mixture of isobutylene and n-butenes and t-butyl alcohol which are preferably diluted with an inert gas. Suitable inert gases include nitrogen, steam and carbon dioxide. In particular, steam favorably influences the reaction by increasing the yield of product.

Molecular oxygen is used as the oxidant in the process of this invention. Air is preferably used from an economic viewpoint. If necessary, the oxidant can be air enriched with pure oxygen. The concentration of oxygen in the feed gas can be varied within the range of 1 to 20% by volume. The concentration of isobutylene, n-butenes or t-butyl alcohol in the feed gas can also be varied within the range of 1 to 20% by volume.

The oxidation reaction is conducted under a pressure ranging from atmospheric pressure to several atmospheres, and the reaction temperature is selected within the range of 200° to 450° C., particularly from 250° to 400° C. The contact time preferably ranges from 0.5 to 10 seconds. The reaction may be conducted in either a fixed bed or a fluidized bed.

Having now generally described the invention, a further understanding can be obtained by reference to certain specific examples which are provided herein for purposes of illustration only and not intended to be limiting unless otherwise specified. In the examples, the term "parts" is by weight and yield is calculated by the following equation:

$$\text{Yield (\%)} = \frac{\text{Objective title product (moles)}}{\text{Starting material charged (moles)}} \times 100$$

(Objective title product is defined as the total of methacrolein and methacrylic acid or 1,3-butadiene).

EXAMPLE 1

In 200 parts of water were suspended 29.3 parts of a fine powder of antimony trioxide, and a solution of 176.6 parts of ammonium molybdate dissolved in 1000 parts of water was added thereto. Thereafter, a solution of 8.1 parts of cesium nitrate dissolved in 10 parts of water, a solution of 40.4 parts of bismuth nitrate dissolved in 50 parts of 10% nitric acid, a solution of 101 parts of ferric nitrate and 145.4 parts of nickel nitrate dissolved in 500 parts of water and 4.62 parts of finely powdered selenium dioxide were added to the mixture. Finally 20 parts of silica were added to the mixture in the form of a silica sol. The slurry obtained was evaporated to dryness, dried at 120° C., pelletted, and then calcined at 500° C. for 6 hours under an atmosphere of air. The composition of the catalyst obtained was $Mo_{12}Sb_2Bi_1Fe_3Ni_6Cs_{0.5}Se_{0.5}$, as expressed in atomic ratios.

The catalyst obtained was packed in a fixed bed reaction vessel and maintained at 360° C., and a gaseous mixture comprising 5% t-butyl alcohol, 12% oxygen, 48% nitrogen and 35% steam (all in volume %) was fed into the reaction vessel at a contact time of 3.6 seconds. The reaction gas discharged was analyzed by gas chromatography and the results obtained showed that the total yield of methacrolein and methacrylic acid was 83.0%.

EXAMPLES 2-26

The catalysts shown in Table I were prepared in the same manner as described in Example I, and were used for the oxidation of t-butyl alcohol under the same conditions as described in Example I except for the reaction temperatures which are also shown in the table. The results are also shown in Table I.

Table I

| Example No. | Catalyst Composition (atomic ratio) | Reaction Temp. (°C.) | Total Yield of Methacrolein and Methacrylic acid (%) |
|---|---|---|---|
| 2 | $Mo_{12}Sb_2Bi_1Fe_3$ $Ni_6Cs_{0.5}V_{0.5}$ | 340 | 83.0 |
| 3 | $Mo_{12}Sb_2Bi_1Fe_3$ $Ni_6Cs_{0.5}Ru_{0.5}$ | 330 | 82.5 |
| 4 | $Mo_{12}Sb_2Bi_1Fe_3$ $Ni_6Cs_{0.5}Te_{0.5}$ | 360 | 84.0 |
| 5 | $Mo_{12}Sb_2Bi_1Fe_3$ $Ni_6Cs_{0.5}Mg_{0.5}$ | 355 | 83.5 |
| 6 | $Mo_{12}Sb_2Bi_1Fe_3$ $Ni_6Cs_{0.5}Cr_1$ | 350 | 83.5 |
| 7 | $Mo_{12}Sb_2Bi_1Fe_3$ $Ni_6Cs_{0.5}Mn_1$ | 350 | 83.0 |
| 8 | $Mo_{12}Sb_2Bi_1Fe_3$ $Ni_6Cs_{0.5}Zn_1$ | 350 | 83.0 |
| 9 | $Mo_{12}Sb_2Bi_1Fe_3$ $Ni_6Cs_{0.5}Nb_1$ | 355 | 83.5 |
| 10 | $Mo_{12}Sb_2Bi_1Fe_3$ $Ni_6Cs_{0.5}Cd_1$ | 355 | 83.0 |
| 11 | $Mo_{12}Sb_2Bi_1Fe_3$ $Ni_6Cs_{0.5}Ta_1$ | 355 | 83.0 |
| 12 | $Mo_{12}Sb_2Bi_1Fe_3$ $Ni_6Cs_{0.5}Se_{0.5}Te_{0.5}$ | 360 | 84.0 |
| 13 | $Mo_{12}Sb_2Bi_1Fe_3$ $Ni_6N_{0.5}Se_{0.5}Ga_{0.5}$ | 350 | 82.0 |
| 14 | $Mo_{12}Sb_4Bi_1Fe_1$ $Ni_7Rb_{0.5}Te_{0.5}$ | 360 | 82.0 |
| 15 | $Mo_{12}Sb_4Bi_1Fe_1$ $Ni_8K_{0.3}Cs_{0.3}Zn_{0.5}Mg_{0.5}$ | 360 | 83.5 |
| 16 | $Mo_{12}Sb_6Bi_{0.5}Fe_2$ $Ni_6K_{0.3}Cs_{0.3}Se_{0.5}Ga_{0.5}$ | 365 | 83.5 |
| 17 | $Mo_{12}Sb_2Bi_2Fe_2$ $Ni_6Co_2Cs_{0.5}Zn_{0.5}$ | 360 | 84.0 |
| 18 | $Mo_{12}Sb_2Bi_2Fe_2$ $Ni_6Co_2K_{0.5}Tl_{0.5}Zn_{0.5}$ | 360 | 83.0 |
| 19 | $Mo_{12}Sb_2Bi_2Fe_2$ $Ni_6Co_2Cs_{0.5}Se_{0.5}$ | 360 | 83.5 |
| 20 | $Mo_{12}Sb_2Bi_2Fe_2$ $Ni_6Co_2Cs_{0.5}Nb_{0.5}$ | 350 | 83.0 |
| 21 | $Mo_{12}Sb_2Bi_2Fe_2$ $Ni_6Co_2Rb_{0.5}V_{0.5}Zn_{0.5}$ | 350 | 83.0 |
| 22 | $Mo_{12}Sb_2Bi_2Fe_2$ $Ni_6Co_2K_{0.3}Rb_{0.3}Ru_{0.5}Zn_{0.5}$ | 340 | 83.0 |
| 23 | $Mo_{12}Sb_4Bi_1Fe_3$ $Ni_4Co_1K_{0.5}Rb_{0.2}Zn_{0.5}$ | 360 | 83.0 |
| 24 | $Mo_{12}Sb_8Bi_{0.5}Fe_4$ $Ni_5Sn_1Cs_{0.5}Zn_{0.5}Mn_{0.5}$ | 360 | 84.0 |
| 25 | $Mo_{12}Sb_2Bi_1Fe_3$ $Ni_6Sn_1K_{0.5}Mg_1$ | 350 | 83.0 |
| 26 | $Mo_{12}Sb_2Bi_1Fe_3$ $Ni_6Sn_1Rb_{0.5}Mg_1$ | 350 | 83.0 |

EXAMPLES 27-29

The catalysts shown in Table II prepared in the same manner as described in Example I and were used for the oxidation of isobutylene. The starting gaseous mixture containing 5% by volume isobutylene, 12% by volume oxygen, 48% by volume nitrogen and 35% by volume steam was fed into the reaction vessel under the same conditions as described in Example I except for the reaction temperatures which are also shown in the table. The results are shown in Table II.

Table II

| Example No. | Catalyst Composition (Atomic ratio) | Reaction Temp. (°C.) | Total Yield of Methacrolein and Methacrylic Acid |
|---|---|---|---|
| 27 | $Mo_{12}Sb_2Bi_1Fe_3$ $Ni_6Cs_{0.5}Se_{0.5}$ | 360 | 82.5 |
| 28 | $Mo_{12}Sb_2Bi_1Fe_3$ $Ni_6Cs_{0.5}Mg_1$ | 355 | 82.0 |
| 29 | $Mo_{12}Sb_2Bi_2Fe_2$ $Ni_6Co_2Cs_{0.5}Zn_{0.5}$ | 360 | 83.0 |

EXAMPLES 30-32

The catalysts of Examples 27, 28 and 29 were used for the oxidation of n-butene. The feed gas comprises 5% by volume n-butene-1, 12% by volume oxygen, 48% by volume nitrogen and 35% by volume steam. The oxidation reactions were conducted under the same conditions as described in Examples 27, 28 and 29. The results are shown in Table III.

Table III

| Example No. | Catalyst Composition (atomic ratio) | Reaction Temp. (°C.) | Yield of 1,3-butadiene |
|---|---|---|---|
| 30 | $Mo_{12}Sb_2Bi_1Fe_3$ $Ni_6Cs_{0.5}Se_{0.5}$ | 360 | 78.0 |
| 31 | $Mo_{12}Sb_2Bi_1Fe_3$ $Ni_6Cs_{0.5}Mg_1$ | 355 | 79.0 |
| 32 | $Mo_{12}Sb_2Bi_2Fe_2$ $Ni_6Co_2Cs_{0.5}Zn_{0.5}$ | 360 | 78.0 |

EXAMPLES 33-35

The catalysts of Examples 27, 28 and 29 were used for the oxidation of a mixture of isobutylene and n-butene. The feed gas comprised 2.5% isobutylene, 2.5% n-butene, 12% oxygen, 48% nitrogen and 35% steam (all by volume). The oxidation reactions were conducted under the same conditions as described in Examples 27, 28 and 29. The results of the experiments are summarized in Table IV.

Table IV

| Example No. | Catalyst Composition (Atomic Ratio) | Reaction Temp. (°C.) | Total Yield of Methacrolein and Methacrylic Acid (%) | Yield of 1,3-butadiene (%) |
|---|---|---|---|---|
| 33 | The catalyst of Example 27 | 360 | 83.0 | 78.0 |
| 34 | The catalyst of Example 28 | 355 | 83.5 | 79.0 |
| 35 | The catalyst of Example 29 | 360 | 83.0 | 78.0 |

CONTROL EXPERIMENTS 1 to 10

Catalysts of the compositions shown in the following table were prepared and were used for the oxidation of t-butyl alcohol or isobutylene under the same conditions as described in Examples 1 or 27 except for the reaction temperature. The results are shown in Table V.

Table V

| Control No. | Catalytic Composition (Atomic ratio) | Reactant | Reaction Temp. (°C.) | Total Yield of Methacrolein and Methacrylic Acid (%) |
|---|---|---|---|---|
| 1 | $Mo_{12}Sb_2Bi_1Fe_3$ $Ni_6Cs_{0.5}$ | t-butyl alcohol | 360 | 79.0 |
| 2 | $Mo_{12}Sb_2Bi_1Fe_3$ $Ni_6Cs_{0.5}$ | isobutylene | 360 | 78.0 |
| 3 | $Mo_{12}Bi_1Fe_3Ni_6$ $Cs_{0.5}Se_{0.5}$ | t-butyl alcohol | 360 | 69.0 |
| 4 | $Mo_{12}Bi_1Fe_3Ni_6$ $Cs_{0.5}Mg_1$ | t-butyl alcohol | 355 | 63.0 |
| 5 | $Mo_{12}Bi_1Fe_3Ni_6$ $Cs_{0.5}$ | t-butyl alcohol | 360 | 65.0 |
| 6 | $Mo_{12}Sb_2Bi_1Fe_3$ $Ni_6Mg_1$ | t-butyl alcohol | 355 | 63.0 |
| 7 | $Mo_{12}Sb_2Bi_2Fe_2$ $Ni_6Co_2Cs_{0.5}$ | t-butyl alcohol | 360 | 80.0 |
| 8 | $Mo_{12}Sb_2Bi_2Fe_2$ $Ni_6Co_2Cs_{0.5}$ | isobutylene | 360 | 79.0 |
| 9 | $Mo_{12}Bi_2Fe_2Ni_6$ $Co_2Cs_{0.5}Zn_{0.5}$ | t-butyl alcohol | 360 | 69.0 |
| 10 | $Mo_{12}Bi_2Fe_2Ni_6$ $Co_2Cs_{0.5}$ | t-butyl alcohol | 360 | 65.0 |

Having now fully described the invention it will be apparent to one of ordinary skill in the art that many changes and modifications can be made thereto without departing from the spirit or scope of the invention as set forth herein.

What is claimed as new and intended to be covered by letters patent is:

1. In a process for catalytically oxidizing isobutylene in the gas phase with molecular oxygen at a temperature of 200° to 450° C. to methacrolein and methacrylic acid, the improvement comprising: oxidizing isobutylene over a calcined catalyst consisting essentially of:

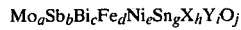

$$Mo_aSb_bBi_cFe_dNi_eSn_gX_hY_iO_j$$

wherein X is at least one metal selected from the group consisting of potassium, rubidium, cesium and thallium, and Y is at least one metal selected from the group consisting of magnesium, chromium, manganese, zinc, niobium, cadmium and tantalum, wherein subscripts a to j are the atomic ratios of each component and a is 12, b=0.2 to 20, c=0.2 to 12, d=0.2 to 12, e=0.2 to 12, g=0 to 20, h=0.01 to 4, i.=0.01 to 4, and j is a value determined by the valencies of the elements in the catalyst.

2. The process of claim 1, wherein Y is magnesium.

3. The process of claim 1, wherein Y is a combination of magnesium and zinc.

4. The process of claim 1, wherein Y is at least one metal selected from the group consisting of chromium, manganese, zinc, niobium, cadmium and tantalum.

5. The process of claim 4, wherein Y is zinc.

6. The process of claim 4, wherein Y is a combination of zinc and manganese.

* * * * *